US009233188B2

(12) United States Patent
Vogt

(10) Patent No.: US 9,233,188 B2
(45) Date of Patent: Jan. 12, 2016

(54) POLYMETHYLMETHACRYLATE BONE CEMENT

(71) Applicant: HERAEUS HOLDING GMBH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 14/078,568

(22) Filed: Nov. 13, 2013

(65) Prior Publication Data

US 2014/0135418 A1    May 15, 2014

(30) Foreign Application Priority Data

Nov. 13, 2012 (DE) .......................... 10 2012 022 134

(51) Int. Cl.
*A61L 24/06* (2006.01)
*A61L 27/16* (2006.01)

(52) U.S. Cl.
CPC .................. *A61L 24/06* (2013.01); *A61L 27/16* (2013.01); *A61L 2430/02* (2013.01)

(58) Field of Classification Search
CPC ..... A61L 24/06; A61L 27/16; A61L 2430/02; C08L 33/10
USPC .......................................................... 523/105
See application file for complete search history.

(56) References Cited

U.S. PATENT DOCUMENTS

| 4,171,544 | A | 10/1979 | Hench et al. |
| 4,588,583 | A | 5/1986 | Pietsch et al. |
| 5,336,699 | A | 8/1994 | Cooke et al. |
| 5,750,590 | A * | 5/1998 | Schaefer et al. ............... 523/115 |
| 5,968,999 | A | 10/1999 | Ramp et al. |
| 6,017,982 | A | 1/2000 | Akinmade |
| 7,259,210 | B2 | 8/2007 | Puckett, Jr. et al. |
| 8,022,130 | B2 * | 9/2011 | Nowak et al. .................. 524/493 |
| 8,598,251 | B2 | 12/2013 | Vogt et al. |
| 8,658,713 | B2 | 2/2014 | Nakamura et al. |
| 8,791,172 | B2 | 7/2014 | Vogt et al. |
| 8,829,073 | B2 | 9/2014 | Nies |
| 2002/0022677 | A1 | 2/2002 | Teramae et al. |
| 2006/0041033 | A1 | 2/2006 | Bisig et al. |
| 2007/0196509 | A1 | 8/2007 | Riman et al. |
| 2009/0105366 | A1 | 4/2009 | Vogt et al. |
| 2011/0054392 | A1 | 3/2011 | Nies |
| 2011/0183932 | A1 | 7/2011 | Vogt et al. |
| 2011/0287067 | A1 | 11/2011 | Stewart |
| 2011/0313078 | A1 | 12/2011 | Vogt et al. |
| 2012/0009327 | A1 | 1/2012 | Vogt et al. |
| 2012/0046385 | A1 | 2/2012 | Nakamura et al. |
| 2012/0196952 | A1 | 8/2012 | Suzuki |
| 2012/0258159 | A1 | 10/2012 | Vogt |
| 2014/0033970 | A1 | 2/2014 | Vogt et al. |
| 2014/0303275 | A1 | 10/2014 | Vogt et al. |
| 2015/0126641 | A1 | 5/2015 | Suzuki |

FOREIGN PATENT DOCUMENTS

| AU | 2008 227053 A1 | 5/2009 |
| CN | 101678148 A | 3/2010 |
| CN | 102333552 A | 1/2012 |
| DE | 603 07 683 T2 | 5/2008 |
| DE | 10 2010 024 653 A1 | 12/2011 |
| EP | 2 492 289 A1 | 8/2012 |
| EP | 249 2289 A1 | 8/2012 |
| JP | 2001 302429 A | 10/2001 |
| JP | 2006 513760 A | 4/2006 |
| JP | 2009 101159 A | 5/2009 |
| JP | 2011 152419 A | 8/2011 |
| JP | 2012 005829 A | 1/2012 |
| JP | 2012 011199 A | 1/2012 |
| JP | 2012 040213 A | 3/2012 |
| JP | 2012 219097 A | 11/2012 |
| WO | 01 76649 A1 | 10/2001 |
| WO | 2004 071543 A1 | 8/2004 |
| WO | 2008 032322 A2 | 3/2008 |
| WO | 2011 117519 A1 | 9/2011 |
| WO | 2011 141889 A1 | 11/2011 |
| WO | 2012 058305 A2 | 5/2012 |

OTHER PUBLICATIONS

German Office Action dated Jul. 4, 2013.
Patent Examination Report No. 1 issued in corresponding Australian Patent Application No. 2013248210 on Apr. 17, 2014.
Notice of Reasons for Rejection issued in corresponding Japanese Patent Application No. 2013-226422 on Jan. 13, 2015.
Abstract of JP S 54135496: Florida State University: et al. Oct. 20, 1979.
Canadian Office Action dated Apr. 8, 2015.
First Chinese Office Action and Search Report issued Apr. 24, 2015 in corresponding application 201310569478.1 and English translation.

* cited by examiner

*Primary Examiner* — Tae H Yoon
(74) *Attorney, Agent, or Firm* — Norris McLaughlin & Marcus, P.A.

(57) ABSTRACT

The subject matter of the invention is a curable composition for use as bone cement, in particular for augmentation of osteoporotic bone tissue, comprising at least one organic polymer and at least one monomer for radical polymerization, at least one particulate inorganic additive having a BET surface of at least 40 $m^2/g$, whereby the additive comprises covalently bound hydroxyl groups, whereby the composition further comprises at least one fatty acid ester or a mixture of fatty acid esters. Another subject matter of the invention is the use of said composition for augmentation of osteoporotic bone tissue and particularly preferably for vertebroplasty, kyphoplasty, and augmentation of drill holes in osteoporotic bone tissue, as well as a kit for producing said composition.

18 Claims, No Drawings

POLYMETHYLMETHACRYLATE BONE CEMENT

This application claims priority of German Patent Application No. 10 2012 022 134.7, filed Nov. 13, 2012, the entire contents of which are incorporated herein by reference.

The subject matter of the invention is a curable composition for use as bone cement, in particular for augmentation of osteoporotic bone tissue, comprising at least one organic polymer and at least one monomer for radical polymerisation, at least one particulate inorganic additive having a BET surface of at least 40 m²/g, whereby the additive comprises covalently bound hydroxyl groups, whereby the composition further comprises at least one fatty acid ester or a mixture of fatty acid esters. Another subject matter of the invention is the use of said composition for augmentation of osteoporotic bone tissue and particularly preferably for vertebroplasty, kyphoplasty, and augmentation of drill holes in osteoporotic bone tissue, as well as a kit for producing said composition. The composition according to the invention preferably is a polymethylmethacrylate cement.

Polymethylmethacrylate bone cements (PMMA bone cements) have been known for decades and are based on the ground-breaking work of Sir Charnley (Charnley, J.: "*Anchorage of the femoral head prosthesis of the shaft of the femur*"; J. Bone Joint Surg. 42 (1960) 28-30). The basic structure of PMMA bone cements has remained the same ever since. PMMA bone cements consist of a liquid monomer component and a powder component. The monomer component generally contains the monomer, methylmethacrylate, and an activator (for example N,N-dimethyl-p-toluidine) dissolved therein. The powder component comprises one or more polymers that are made by polymerisation, preferably by suspension polymerisation, based on methylmethacrylate and co-monomers, such as styrene, methylacrylate or similar monomers, as well as a radiopaquer and an initiator, (e.g. dibenzoylperoxide). Mixing the powder component and the monomer component, the polymers of the powder component in the methylmethacrylate swell which generates a dough that can be shaped plastically. Simultaneously, the activator, N,N-dimethyl-p-toluidine, reacts with dibenzoylperoxide which disintegrates and forms radicals in the process. The radicals thus formed trigger the radical polymerisation of the methylmethacrylate. Upon advancing polymerisation of the methylmethacrylate, the viscosity of the cement dough increases until the cement dough solidifies and thus is cured.

Vertebral body fractures occur often in elderly patients afflicted by osteoporosis. Some of said vertebral body fractures cause significant pain due to nerve compression. Galibert et al. were the first in 1987 to describe the treatment of vertebral bodies by augmentation with bone cement coining the term of "percutaneous vertebroplasty" (Galibert P., Deramond H., Rosat P., Le-Gars D. (1987) Note preliminaire sur le traitement des angiomes vertebraux par vertebroplastie acrylique percutanee. [Preliminary note on the treatment of vertebral angioma by percutaneous acrylic vertebroplasty] Neurochirurgie 33: 166-168.) Subsequently, further methods for augmentation of fractured vertebral bodies were developed, whereby kyphoplasty has become the most widespread of these thus far. It involves that the fractured vertebral body is first erected by means of a balloon and then augmented by means of cement.

Currently, it is customary to use inorganic calcium phosphate cements and, generally, PMMA bone cement for augmentation of osteoporotic vertebral bodies. This often involves the use of low viscosity PMMA cements, since these are easier to apply. In this context, the PMMA cements are injected into the vertebral bodies using syringes, screw systems or hydraulic systems while applying relatively high pressures. This may be associated with serious complications if the cement flows out of the implantation area and into the efferent veins, the paravertebral space or the spinal canal.

A number of developments aimed at reducing these risks have become known.

WO2011117519 discloses a bone cement that is made up of a powder component and a gel-like monomer component. The powder component contains a polymer that can be swelled in the monomer, an initiator, and a radiopaquer. The gel-like component is made up of the monomer, a polymer that is dissolved in the monomer and has a molar mass in excess of 1,000,000 Dalton, and an accelerator. Right after the powder component and the gel-like monomer component are mixed, the thickener effect of the polymer dissolved in the gel-like monomer component causes the cement dough consistency to be similar to that of a highly viscous PMMA bone cement. A highly viscous cement dough can be expected to show little tendency to flow, which reduces the risk of undesired leakage of cement from the vertebral bodies.

A different concept is disclosed in WO2008/032322. In this concept, high viscosity of the cement dough is attained right after the powder component is mixed with the liquid monomer component by having two polymers of different molar mass being present in the cement powder. A first polymer has a mass-averaged molar mass (MW) of 150,000-300,000 Dalton and a second polymer has a mass-averaged molar mass (MW) in excess of 3,000,000 Dalton. The lower molecular weight polymer swells or dissolves more rapidly in the monomer liquid than the higher molecular weight polymer. This makes the lower molecular weight polymer act as a thickener. The cement dough formed is thus made viscous.

A particularly interesting approach to preventing the leakage of cement from vertebral bodies is described in WO2012058305. Here, a sealant is introduced into the vertebral body and reacts with calcium ions, which are always present in bone tissue, by forming a sealing layer and thus sealing all gaps and other openings in vertebral bodies. Sodium alginate is proposed as the sealant. Sodium alginate reacts with calcium ions to form a gel.

Increasing the viscosity of the PMMA cements used for augmentation is certainly one way to reduce the risk of undesired cement leakage. However, the increase in viscosity of the cement dough is associated with an increase in the flow resistance upon introduction of the cement through cannulas. This means that this type of cement require application systems, such as hydraulic systems, that can generate very high pressures to be able to press the cement dough through the cannulas.

It was an object of the invention to develop a composition for use as bone cement, in particular a PMMA cement for vertebroplasty and kyphoplasty, that is non-dripping, if possible immediately, after the powder component and the monomer liquid are mixed. Moreover, the invention was to provide a composition for use as bone cement that is thixotropic during the processing phase and shows reduced adhesion to surfaces, in particular the curable composition is to show reduced wetting behaviour on surfaces. It was another object of the invention to provide a composition for use as bone cement that has a prolonged processing phase after the components are mixed. The composition for use as bone cement, also referred to as cement dough, should best be flowable only when exposed to mechanical stress. In the absence of mechanical stress, the curable composition should show little tendency to flow. Moreover, the composition, in particular in the form of PMMA cement, should adhere very little to steel or other metal surfaces in order to render the cement easier to inject through metal cannulas. The advantages of the curable composition showing thixotropic behaviour are, on the one hand, that the composition can be introduced more easily under pressure exposed to the shearing effect in a cannula, and, on the other hand, that the undesired leakage of cement after the composition is introduced into the cavity to be filled in the absence of a shearing effect is reduced.

The object of the invention was met according to the subject matter described hereinbelow.

According to one embodiment, the composition according to the invention is a polymethylmethacrylate cement, comprising a powder component and a liquid monomer component, whereby the composition comprises at least one particulate inorganic additive having a BET surface of at least 40 $m^2/g$ that comprises hydroxyl groups covalently bound to the particles, and contains, in addition, at least one fatty acid ester that is liquid at room temperature.

The rationale of the invention is to add an additive with a thixotropic effect and an anti-adhesive, biocompatible and/or absorbable additive to a composition for use as bone cement. In this context, the present document refers to composition and bone cement as synonymous terms. Surprisingly, the pasty composition in the form of a cement dough was non-dripping right after the powder component and the liquid monomer component were mixed, and was flowable during the processing phase only when exposed to mechanical stress and showed little tendency to flow in the absence of mechanical stress.

Just as surprising was the finding that adding fatty acid esters that are liquid at room temperature as a component of the composition for use as bone cement makes the cement dough obtained show less adhesion to metal surfaces as compared to the non-modified curable composition. It was also surprising that the two additives are compatible with each other in the cement.

The subject matter of the invention is a composition for use as bone cement, comprising at least one organic polymer and at least one polymerisable monomer, whereby the composition can be cured and comprises
  at least one monomer for radical polymerisation;
  at least one particulate inorganic additive having a BET surface of at least 40 $m^2/g$, whereby the additive comprises covalently bound hydroxyl groups; and
  at least one fatty acid ester or a mixture of fatty acid esters.

According to the invention, a polymer that is soluble in said monomer is used as organic polymer. The curable composition according to the invention is also referred to by its synonymous terms of cement dough, cement or bone cement. According to a particularly preferred embodiment, the composition is a thixotropic and curable fluid or a thixotropic and curable paste. Preferably, a neutral oil, MCT oil (CAS no. 73398-61-5), a mixture of medium-chain fatty acids (triglycerides), capric acid specifically and caprylic acid of natural origin are also considered to be a mixture of fatty acid esters.

In order to attain the effect according to the invention, i.e. the reduced adhesion to preferably metallic or plastic surfaces, and to concurrently obtain a composition that is flowable preferably under elevated pressure only, a combination of additives had to be found that allowed the desired properties to be set specifically.

Surprisingly, it was found that adding a fraction of at least one fatty acid ester or of a mixture of fatty acid esters to a bone cement composition clearly reduces the adhesion of the composition to surfaces during the processing phase and concurrently has no negative effects on the curing of the composition after transfer into the bone cavity. The inorganic additive exerts its effect in the composition during the production phase of the composition, during the processing phase and during the curing phase. The inorganic additive has to meet a number of requirements in this context: the additive and the further components of the composition, in particular the liquid components, such as the fatty acid esters and/or the monomers, need to rapidly form a paste that is preferably no longer flowable when exposed to standard pressure, but becomes flowable when exposed to clearly higher pressure when it is dispensed through a cannula of a syringe during the processing phase, while the viscosity of the composition clearly decreases when exposed to pressure. After pressure relief, basically to standard pressure (approx. 1013.25 hPa), especially after dispensation of the composition into a bone cavity, the curable composition is to re-assume increased viscosity and be non-flowable during the curing phase. Combining, according to the invention, fatty acid esters and inorganic additives with HO groups of a defined BET surface allowed to provide a composition that meets the requirements specified above.

It was also surprising that the two added additives had only a minimal influence on the mechanical properties of the cured composition, i.e. of the cured PMMA cement, as compared to a conventional PMMA cement, and that this allows a PMMA cement to be obtained that meets the mechanical requirements of ISO583.

The, according to the invention, at least one fatty acid ester or mixture of fatty acid esters preferably comprises (i) an ester from converting at least one fatty acid and a mono-alcohol, diol, triol or polyol each having 1 to 15 C atoms, in particular having 1 to 4 C atoms, particularly preferably having C1 to C4 alkyl groups, or a polyetherpolyol, (ii) a naturally occurring fatty acid ester or a fatty acid ester of natural origin, and (iii) a mixture containing fatty acid esters from (i) and (ii). It is particularly preferred in this context that the at least one fatty acid ester or the mixture of fatty acid esters is liquid at room temperature between 18 to 35° C., in particular between 20 and approx. 25° C. or at body temperature of approx. 36 to 37.5° C. (at standard pressure).

Fatty acid esters are understood to be fatty acid esters that comprise at least one fatty acid ester group, for example of an oleic acid, and, optionally, further esters other than fatty acid esters, such as esters of dicarboxylic acid comprising, in particular, 1 to 18 C atoms, preferably of succinic acid.

Proven as particularly preferred as fatty acid esters or mixtures of fatty acid esters are fatty acid alkyl esters, in particular a fatty acid alkyl ester having 1 to 15 C atoms in the alkyl chain of the ester, preferably having 1 to 4 C atoms or 3 C atoms of glycerol, and preferably a fatty acid having 1 to 30 C atoms in the fatty acid residue, in particular having 1 to 20 C atoms, preferably 3 to 20 C atoms, whereby saturated fatty acids are preferred. Also proven to be preferred as fatty acid esters or mixtures of fatty acid esters are fatty acid alkyl esters, at least one triglyceride or a mixture containing at least one of the above-mentioned compounds. In this context, the fatty acid esters or the mixture of fatty acid esters can generally comprise saturated fatty acids and/or unsaturated fatty acids, whereby saturated fatty acids have proven to be preferred.

Preferred fatty acid esters comprise fatty acid methyl esters (FAME) of plant fats since these are usually liquid at room temperature and standard pressure. Triacylglycerols having three fatty acids are also well-suited. A well-known triglyceride, coconut oil consists mainly of triglycerides and contains saturated fatty acid residues derived from caprylic, lauric, capric, palmitic, stearic and myristic acid.

Another subject matter of the invention are polymethylmethacrylate cements, comprising a powder component and at least one liquid monomer component, whereby the composition comprises at least one particulate inorganic additive having a BET surface of at least 40 m²/g that comprises hydroxyl groups covalently bound to the particles, and at least one fatty acid ester that is liquid at room temperature or a mixture of fatty acid esters.

In order to prevent undesirable diffusion into the body or abrasion, a particularly pure composition is provided in which the content of the at least one organic polymer is more than or equal to 99.5% by weight, in particular more than or equal to 99.8% by weight, even more preferably more than or equal to 99.9% by weight relative to the entire polymer composition, whereby the foreign compound impurities in the polymer preferably account for less than or equal to 0.5% by weight, in particular less than or equal to 0.2% by weight, even more preferably less than or equal to 0.1% by weight. In this context, the content of organic solvents, in particular, is less than or equal to 0.5% by weight.

It is also preferred that the content of the polymerisable monomer also is more than or equal to 99.1% by weight, in particular 99.5% by weight, relative to the total monomer composition, in particular is more than or equal to 99.8% by weight, particularly preferably is more than or equal to 99.9% by weight, whereby the foreign compound impurities in the monomer concurrently account for less than or equal to 0.5% by weight, in particular less than or equal to 0.2% by weight, preferably less than or equal to 0.1% by weight.

The content of the at least one particulate inorganic additive is just as relevant. Its additive content, in particular of $SiO_2$, preferably is more than or equal to 99.5% by weight and the foreign compound impurities in the additive preferably account for less than or equal to 0.5% by weight. The content of possibly cement-decomposing substances, such as free acids or chlorides, should be low due to the long indwelling time of the bone cements in the body in order to provide bone cements with a long service life.

For the reasons specified above, a preferred fatty acid ester or a mixture of fatty acid esters has a fatty acid ester content of more than or equal to 99.5% by weight relative to the total composition, and the foreign compound impurities in the fatty acid esters or mixtures thereof account for less than or equal to 0.5% by weight.

Particulate inorganic additives that are suitable according to the invention comprise HO—Si groups that are covalently bound to the particles (silanol groups). Said hydroxyl groups that are arranged on the surface of the particles allow hydrogen bonds between the filling agent particles to form, which can be released reversibly through the action of mechanical or thermal energy.

The particulate inorganic additive is selected from the group of pyrogenic silicon oxide, pyrogenic mixed metal-silicon oxides, bentonite, montmorillonite, and a mixture containing at least two of said additives.

Moreover, it is also feasible to use pyrogenic silicon dioxide made hydrophobic. The hydrophobic silicon dioxide can be produced according to the prior art through treating pyrogenic silicon dioxide with dialkyldichlorosilanes (e.g. dimethyldichlorosilane).

Pyrogenic silicon dioxide with a BET surface of at least 40 m²/g, particularly preferably of 200 m²/g, and most preferably of 300 m²/g, is particularly preferred as particulate inorganic filling agent. Said pyrogenic silicon dioxide is commercially available by the brand name of Aerosil® having specific BET surfaces of 50 m²/g, 90 m²/g, 200 m²/g, and 380 m²/g.

Pyrogenic silicon oxide having a BET surface of at least 200 m²/g is particularly preferred. It is also preferred to use as particulate inorganic additive a pyrogenic silicon oxide having a BET surface of at least 300 m²/g. The particulate inorganic additives that are suitable according to the invention preferably comprise primary particles having a mean diameter (D50) of 5 to 9 nm, preferably 6 to 8 nm and especially preferred approx. 7 nm having a specific surface of 270 to 330 m²/g. It is particularly preferred to use as particulate inorganic additive a pyrogenic silicon dioxide having an $SiO_2$ content of more than or equal to 99.8% by weight (of the calcined additive) and a content of chlorides and foreign metal oxides of less than or equal to 0.2% by weight relative to the additive. Especially aluminium oxide, iron oxide, and titanium oxide are considered as foreign metal oxides in the pyrogenic silicon dioxide.

The BET measurement is an analytical procedure for characterisation of the surface of solids by means of gas adsorption. Said determination method is described in DIN ISO 9277:2003-05 (Determination of the specific surface of solids by gas adsorption according to the BET method).

The fatty acid esters or mixtures of fatty acid esters are preferably selected from the group of the saturated and the unsaturated fatty acid esters, whereby (i) the group of the saturated fatty acid esters comprises: esters of caprylic acid (octanoic acid), capric acid (decanoic acid), lauric acid (dodecanoic acid), myristic acid (tetradecanoic acid), palmitic acid (hexadecanoic acid), and stearic acid (octadecanoic acid), and
(ii) the group of the unsaturated fatty acid esters comprises: esters of linolic acid, alpha-linolenic acid, gamma-linolenic acid, calendula acid, punicic acid, alpha-elaeostearic acid, beta-elaeostearic acid, arachidonic acid, timnodonic acid, clupanodonic acid, cervonic acid, myristoleic acid, undecylenic acid, palmitoleic acid, petroselic acid, oleic acid, elaidic acid, vaccenic acid, gadoleic acid, icosenic acid, cetoleic acid, erucic acid, nervonic acid, whereby the esters in (i) and (ii) are derived from conversion of one or more fatty acids from (i) and/or (ii) with a mono-alcohol, diol, triol or polyol, each independently having 1 to 15 C atoms, in particular having 1 to 8 C atoms, such as glycerol, methanol, ethanol, propanol, butanol or a polyetherpolyol.

Methyl esters, ethyl esters, n-propyl esters, isopropyl esters or glycerides, in particular triglycerides, are preferred. The esters of saturated fatty acids that are liquid at room temperature have proven to be particularly well-suited. This includes, in particular, the methyl esters, ethyl esters, n-propyl esters, and isopropyl esters as well as the glycerides of caprylic acid (octanoic acid), capric acid (decanoic acid), lauric acid (dodecanoic acid), myristic acid (tetradecanoic acid), palmitic acid (hexadecanoic acid), and stearic acid (octadecanoic acid) as well as mixtures thereof as fatty acid esters that are liquid at room temperature. Liquid depot fats or fatty acid esters that are liquid at room temperature or mixtures thereof are well-suited as well.

The following fatty acid esters or mixtures thereof that are liquid at room temperature have proven to be particularly well-suited: Glycerol-tri-caprylate (glycerol-tri-octoate), glycerol-tri-caprinate (glycerol-tri-decanoate). The purity and good tolerability of said fatty acids is advantageous as well. Mixtures of said fatty acid esters are commercially available as Mygliol® 810. Moreover, propylene glycol dicaprylate and propylene dicaprate can be used as liquid fatty acid ester. Said esters are commercially available as Mygliol® 840. Moreover, neutral oils of similar structure, additionally containing succinic acid and/or oleic acid, are also well-suited as fatty acid esters. Also commercially available are neutral oils or MCT triglycerides that differ in the percentages of the two fatty acids, caprinic acid (C10:0) and caprylic acid (C8:0), in the composition, inter alia Mygliol 812® made by Sasol, Myritol 312® made by Cognis, and Tegosoft® CT made by Evonik. All these are lipids based on approx. 50-65% caprylic acid (C8:0) and approx. 30-45% capric acid (C10:0); very small fractions of caproic acid (C6:0), lauric acid (C12:0), and myristic acid (C14:0) are also present.

The bone cements according to the invention are compositions comprising at least one organic polymer or mixtures of organic polymers, which are, in particular, soluble in the monomers, whereby the polymers are polyacrylates, whereby the organic polymer is, in particular, selected from poly(alkyl-2-acrylic acid alkylester), poly(aryl-2-acrylic acid alkylester), poly(arylalkyl-2-acrylic acid alkylester), each independently having 1 to 18 C atoms in the alkyl group, in particular having 1 to 4 C atoms, each independently having 6 to 13 C atoms in the aryl group, in particular having 6, 10, 12 or 13 C atoms, each independently having 6 to 14 C atoms in the arylalkyl group, in particular having 8 to 12 C atoms, and each independently having 1 to 10 C atoms in the alkylester group, in particular having 1 to 4 C atoms, or a mixture comprising at least two of the polymers specified above.

It is particularly preferred for the organic polymer, in particular a polymer that is soluble in the monomer, to be selected from the group of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), copolymers of said compounds, and a mixture of at least two of said polymers, whereby polymethylmethacrylate (PMMA) is used particularly preferably.

A polymer that is soluble in the monomer for radical polymerisation shall be understood to be a polymer of which at least 10 g/l, preferably at least 25 g/l, more preferably at least 50 g/l, and even more preferably at least 100 g/l dissolve in said monomer for radical polymerisation. The polymer that is soluble in the polymerisable monomer can be a homopolymer or a copolymer. Said soluble polymer preferably is a polymer with a mean (by weight) molar mass (Mw) of at least 150,000 g/mol, in particular at least 200,000 g/mol and up to more than or equal to 5,000,000 g/mol. The soluble polymer can, for example, be a polymer or copolymer of a methacrylic acid ester. According to a particularly preferred embodiment, the at least one soluble polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), poly(styrene-co-methylmethacrylate), and a mixture of at least two of said polymers.

The amount of the polymer that is soluble in said monomer for radical polymerisation that is present in the composition according to the invention usually is in a range of 1 to 85% by weight, relative to the total weight of the composition according to the invention. Accordingly, the polymer content of the subsequent pastes A, B, and/or D and of the powder component C can, independent of each other, be 1 to 85% by weight relative to the respective total composition of paste or powder component.

At least one poly(methacrylic acid methylester) (PMMA) and methacrylic acid methylester (MMA) are used as particularly preferred organic polymer and as monomer, respectively, whereby mixtures thereof including further monomers or a copolymer of PMMA can be used just as well.

Polymers, in particular polyacrylates, having a molecular weight (Mw) of preferably more than or equal to 200,000 g/mol are used as polymers that are soluble in the monomers for producing powder components, whereby molecular weights of more than or equal to 500,000 g/mol are preferred. Polymers having a molecular weight of less than or equal to 500,000 g/mol can also be used in pastes. In this context, the suitable molecular weight is determined, on the one hand, by whether a paste or a powder component is being produced and by the further components present in the paste, and by the polymer having to be soluble in the monomer that is used.

The monomers for radical polymerisation used in the composition are preferably selected from at least one alkyl-2-acrylic acid alkylester, aryl-2-acrylic acid alkylester, arylalkyl-2-acrylic acid alkylester, each independently having 1 to 18 C atoms in the linear, branched or cyclic alkyl group, in particular having 1 to 4 C atoms, each independently having 6 to 13 C atoms in the aryl group, each independently having 6 to 14 C atoms in the arylalkyl group, in particular having 8 to 12 C atoms, and each independently having 1 to 20 C atoms in the alkylester group, preferably having 1 to 10 C atoms in the alkylester group, whereby the alkylester group can comprise a linear, branched or cyclic alkyl group, in particular having 1 to 4 C atoms, or be a mixture comprising at least two of the monomers specified above, whereby methacrylic acid methylester, a methacrylic acid ester or an alkylacrylic acid methylester are preferred. Methacrylic acid methylester, such as a methacrylate monomer, in particular a methacrylate monomer that is liquid at a temperature of 25° C. and a pressure of 1,013 hPa, is particularly preferred. Preferably, the monomer for radical polymerisation is not a bisphenol A-derived methacrylic acid ester.

Preferably, the methacrylate monomer is a methacrylic acid ester. Preferably, the methacrylic acid ester is a monofunctional methacrylic acid ester. Preferably, said substance is hydrophobic. The use of hydrophobic monofunctional methacrylic acid esters allows later increases in bone cement volume due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The monomer for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer for radical polymerisation is preferably characterised in that an aqueous solution of the monomer for radical polymerisation has a pH in the range of 5 to 9, preferably in the range of 5.5 to 8.5, even more preferably in the range of 6 to 8, and particularly preferably in the range of 6.5 to 7.5.

According to a particularly preferred embodiment, the methacrylate monomer is a methacrylic acid methylester, methacrylic acid ethylester or a mixture of said two monomers.

Preferably, the paste according to the invention contains an amount of the monomer for radical polymerisation in a range of 15 to 85% by weight, more preferably 20 to 70% by weight, even more preferably 25 to 60% by weight, and particularly preferably 25 to 50% by weight, each relative to the total weight of the paste according to the invention.

A composition according to the invention comprises, aside from the soluble organic polymer, in particular polymethylmethacrylate (PMMA), and the monomer for radical polymerisation, in particular methacrylic acid methylester, the particulate inorganic additive at a concentration of 0.01 to 0.5% by weight, in particular of 0.01 to 0.25% by weight, preferably of 0.02-0.14% by weight, relative to the total composition, and the at least one fatty acid ester that is liquid at room temperature at a concentration of 0.01 to 10.0% by weight, in particular of 0.5 to 8.0% by weight, particularly preferably of 1.0-6.0% by weight, relative to the total composition. According to the invention, the cement dough obtained by mixing the powder component and the liquid monomer component comprises the particulate inorganic additive at a concentration of 0.02-0.14% by weight and the at least one fatty acid ester that is liquid at room temperature at a concentration of 1.0-6.0% by weight in the total composition. In addition to the components mentioned above, a composition according to the invention comprises a radiopaquer, a polymerisation initiator and/or a polymerisation accelerator and, optionally, additional filling agents other than the additive that simply possess a thickening effect.

According to an embodiment of the invention, a kit comprising a paste A and a paste B is claimed, whereby
(a) paste A contains
(a1) at least one monomer for radical polymerisation, in particular at 15 to 85% by weight, preferably at 20 to 70% by weight, more preferably at 25 to 60% by weight, even more preferably at 25 to 50% by weight;
(a2) at least one organic polymer that is soluble in (a1), in particular at 5 to 50% by weight, preferably at 10 to 40% by weight, even more preferably at 20 to 30% by weight; and
(a3) at least one polymerisation initiator, in particular at 0.1 to 10% by weight, preferably at 0.01 to 8% by weight, even more preferably at 0.01 to 5% by weight,
and, optionally, further ingredients, such as radiopaquer and/or filling agent that is insoluble in (a1), each relative to the total weight of paste A; and
(b) paste B contains
(b1) at least one monomer for radical polymerisation, in particular at 15 to 85% by weight, preferably at 20 to 70% by weight, more preferably at 25 to 60% by weight, even more preferably at 25 to 50% by weight;
(b2) at least one organic polymer that is soluble in (b1), in particular at 5 to 50% by weight, preferably at 10 to 40% by weight, even more preferably at 20 to 30% by weight; and
(b3) at least one polymerisation accelerator, in particular at 0.0005 to 0.5% by weight, and, optionally, further ingredients, such as radiopaquer and/or filling agent that is insoluble in (b1), each relative to the total weight of paste B;
and whereby at least one of the pastes A and B comprises as component (a4) and/or (b4) at least one particulate inorganic additive having a BET surface of at least 40 m$^2$/g, whereby the additive comprises covalently bound hydroxyl groups and whereby at least one of the pastes A and B comprises as component (a5) and/or (b5) at least one fatty acid ester or a mixture of fatty acid esters. According to an alternative, each of the pastes can contain a fatty acid ester content.

In this context, each of the pastes can contain the particulate inorganic additive at a concentration of 0.001 to 2% by weight, in particular 0.001 to 1% by weight, such that 0.01 to 0.5% by weight of the additive, in particular from 0.01 to 0.25% by weight, preferably 0.02-0.14% by weight, relative to the total composition can be present in the composition that can be obtained through mixing pastes A and B at a ratio of approximately 1 to 1 (plus/minus 0.5 in either value). Accordingly, the at least one fatty acid ester that is liquid at room temperature also can be present in any of the pastes at a concentration of 0.01 to 30% by weight, in particular 0.01 to 20% by weight, each independent of each other. It is preferable that the fatty acid ester content of the composition that can be obtained by mixing pastes A and B at a ratio of approximately 1 to 1 (plus/minus 0.5 in either value) is 0.01 to 10.0% by weight, in particular 0.5 to 8.0% by weight, particularly preferably 1.0-6.0% by weight, relative to the total composition. The same applies in like manner to the subsequent powder component C and monomer component D, whereby the fatty acid ester is preferably added in appropriate amounts only to monomer component D, in that the composition that can be obtained from C and D contains 0.01 to 10.0% by weight of the at least one fatty acid ester in the total composition. Whereby it is preferred to mix C and D at a ratio of approximately 2:1 to 1:2.

The monomers and polymers defined above are used as monomers and polymers in pastes A and B.

According to a further embodiment, a kit comprising a powder component C and a monomer component D is claimed, whereby the
(c) powder component C contains
(c1) at least one powder-shaped polyacrylate, in particular at 1 to 95% by weight, preferably up to 85% by weight;
(c2) at least one powder-shaped radiopaquer, in particular at 3 to 60% by weight, preferably 3 to 30% by weight; and
(c3) at least one polymerisation initiator, in particular at 0.1 to 10% by weight, preferably at 0.01 to 8% by weight, even more preferably at 0.01 to 5% by weight, and, optionally, further ingredients, such as radiopaquer and/or filling agent that is insoluble in (a1), each relative to the total weight of paste A;
and the
(d) monomer component D contains
(d1) at least one monomer for radical polymerisation, in particular at 15 to 85% by weight, preferably at 20 to 70% by weight, more preferably at 25 to 60% by weight, even more preferably at 25 to 50% by weight;
(d2) optionally, at least one organic polymer that is soluble in (d1), in particular at 5 to 50% by weight, preferably at 10 to 40% by weight, even more preferably at 20 to 30% by weight; and
(d3) at least one polymerisation accelerator, in particular at 0.0005 to 0.5% by weight, and, optionally, further ingredients, such as radiopaquer and/or filling agent that is insoluble in (d1), each relative to the total weight of paste D;
and whereby at least the powder component C or the monomer component D comprises as component (c4) and/or (d4) at least one particulate inorganic additive having a BET surface of at least 40 m$^2$/g, and whereby the additive comprises covalently bound hydroxyl groups and whereby at least the monomer component D or the powder component C comprises as component (c5) and/or (d5) at least one fatty acid ester or a mixture of fatty acid esters. Preferably, monomer component D comprises the at least one fatty acid ester or a mixture of fatty acid esters. An organic polymer in the form of a powder according to the preceding definition is used as powder-shaped polyacrylate, whereby powder-shaped PMMA is preferred. In general, an additive content can be present both in the powder component and in the paste. Preferably, the at least one fatty acid is present in the paste.

In the case of a composition according to the invention that was obtained by combining two pastes A and B or powder component C and monomer component D of a two-component system, said composition preferably contains at least one polymerisation initiator (that was present in the one paste of the two-component system) and at least one polymerisation accelerator (that was present in the other paste of the two-component system).

The monomers and polymers defined above are used as monomers and polymers in pastes A and B.

Usually, paste A and/or B and powder component C and/or monomer component D contain a radiopaquer, each independent of each other.

The above-mentioned pastes A and B can be mixed with each other at any arbitrary ratio, whereby the use of pastes A and B at a ratio of essentially 1:1 for mixing has proven to be preferred, whereby the ratio can vary by plus/minus 50% independent of each other.

Moreover, the compositions, pastes and/or powder components according to the invention can contain at least one polymerisation initiator (which preferably is soluble in the monomer for radical polymerisation), at least one polymerisation accelerator (which preferably is soluble in the monomer for radical polymerisation), at least one polymerisation co-accelerator, if applicable, or at least one polymerisation initiator, at least one polymerisation accelerator, and, if applicable, at least one polymerisation co-accelerator.

In the case of a one-component system being the composition according to the invention, the polymerisation initiator preferably is an activatable polymerisation initiator, e.g. a photoinitiator that is dissolved or suspended in the composition, which is present as a paste, or a photoinitiator system that is dissolved or suspended in the paste. It is feasible just as well to provide an initiator or initiators where it/they are temporarily in contact with the paste, for example in a container part, a dosing facility or a transport cannula. Moreover, in a one-component system, the composition or paste according to the invention can also contain an electrically conductive radiopaquer aside from the activatable polymerisation initiator. Particles made of cobalt, iron, NdFeB, SmCo, cobalt-chromium steel, zirconium, hafnium, titanium, titanium-aluminium-silicon alloys, and titanium-niobium alloys having a particle size of 0.5-500 µm are particularly well-suited in this context. It is feasible to induce eddy currents in said electrically conductive radiopaquer through alternating magnetic fields of a frequency in the range of 500 Hz to 50 kHz which cause the radiopaquer to heat up. Due to heat transmission, the initiator is heated as well and induced to thermally disintegrate.

Conceivable as polymerisation initiator are, in particular, peroxides and barbituric acid derivatives, whereby preferably at least 1 g/l, more preferably at least 3 g/l, even more preferably at least 5 g/l, and particularly preferably at least 10 g/l of the peroxides and barbituric acid derivatives can dissolve(s) in the polymerisable monomer at a temperature of 25° C.

According to the invention, a peroxide is understood to mean compounds that contain at least one peroxo group (—O—O—). The peroxide preferably comprises no free acid groups. The peroxide can be an inorganic peroxide or an organic peroxide, such as, for example, a toxicologically acceptable hydroperoxide. According to a particularly preferred embodiment, the peroxide is selected from the group consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two of these substances.

The barbituric acid derivative preferably is a barbituric acid derivative selected from the group consisting of 1-monosubstituted barbiturates, 5-mono-substituted barbiturates, 1,5-di-substituted barbiturates, and 1,3,5-tri-substituted barbiturates. According to a particular refinement of the paste according to the invention, the barbituric acid derivative is selected from the group consisting of 1,5-di-substituted barbiturates and 1,3,5-tri-substituted barbiturates.

There is no limitation with regard to the type of substituents on the barbituric acid. The substituents can, for example, be aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred. According to a preferred embodiment, the substituents each have a length of 1 to 10 carbon atoms, more preferably a length of 1 to 8 carbon atoms, and particularly preferably a length in the range of 2 to 7 carbon atoms. According to the invention, barbiturates bearing one substituent each at position 1 and position 5 or a substituent at positions 1, 3, and 5 are preferred. According to another preferred embodiment, the barbituric acid derivative is a 1,5-disubstituted barbiturate or a 1,3,5-trisubstituted barbiturate. According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

Heavy metal compounds selected from the group consisting of heavy metal salts and heavy metal complexes are preferred as polymerisation accelerator. Heavy metal compounds that are preferred according to the invention are selected from the group consisting of copper(II) hydroxide, copper(II) methacrylate, copper(II) acetylacetonate, copper (II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two of these substances.

According to another refinement of the composition or paste according to the invention, the polymerisation accelerator is selected from the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, pyromellitic acid diimide, and a mixture of at least two of these substances.

Another advantageous refinement of the invention comprises the use, as polymerisation accelerator, of combinations of heavy metal salts and at least one member of the group comprising N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, and pyromellitic acid diimide. Combinations of two and combinations of three different polymerisation accelerators in this context are disclosed in the scope of the invention.

An advantageous refinement of the invention consists of the composition according to the invention or any of the pastes A, B or D containing at least one polymerisation co-accelerator, if applicable, whereby tertiary amines and amidines are preferred as polymerisation co-accelerators, and whereby N,N-dimethyl-p-toluidine, N,N-bis-hydroxyethyl-p-toluidine, N,N-dimethyl-aniline, 1,8-diazabicyclo[5.4.0-] undec-7-ene, and 1,5-diazabicyclo(4.3.0)-non-5-ene are particularly preferred as co-accelerators.

The composition according to the invention, in particular in the form of a paste, can contain a (total) amount of the polymerisation initiator, polymerisation accelerator, co-polymerisation accelerator or the polymerisation initiator, polymerisation accelerator, and co-polymerisation accelerator of up to 10% by weight, relative to the total weight of the composition according to the invention or, each independent of each other, relative to the total weight of any of the pastes A, B or D.

The composition according to the invention, in particular in the form of a paste, or pastes A, B or D as well as the powder component C can contain further ingredients aside from the components mentioned above.

According to a preferred embodiment of the composition according to the invention or of any of the pastes A, B or D and of powder component C, these can, each independent of each other, contain at least one radiopaquer. The radiopaquer can be a common radiopaquer in this field. Suitable radiopaquers can be soluble or insoluble in the monomer for radical polymerisation. The radiopaquer is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts. Said radiopaquers preferably have a particle diameter in the range of 10 nm to 500 µm. Moreover, conceivable radiopaquers also include esters of 3,5-bis(acetamido)-2,4,6-triiodobenzoic acid, gadolinium compounds, such as gadolinium chelate involving the esters of 1,4,7,10-tetraazacyclododecan-1,4,7,10-tetraacetic acid (DOTA). The radiopaquer concentrations, in particular the zirconium dioxide concentration, in the composition according to the invention or any of the pastes A, B or D as well as in powder component C can, each independent of each other, be in a range of, for example, 3 to 30% by weight relative to the corresponding total composition. Radiopaquers are not considered to be filling agents herein.

According to a further preferred embodiment, the composition according to the invention or any of the pastes specified above can contain at least one colourant. The colourant can be a common colourant in this field and preferably can be a food colourant. Moreover, the colourant can be soluble or insoluble in the at least one monomer for radical polymerisation. According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

According to a further preferred embodiment, the composition according to the invention can contain at least one biocompatible elastomer. Preferably, the biocompatible elastomer is particulate. Preferably, the biocompatible elastomer is soluble in the at least one monomer for radical polymerisation. The use of butadiene as biocompatible elastomer has proven to be particularly well-suited.

According to a further preferred embodiment, the composition according to the invention can contain at least one monomer having adsorption groups. An adsorption group can, for example, be an amide group. Accordingly, the monomer with adsorption group can, for example, be methacrylic acid amide. Using at least one monomer with adsorption groups would allow the binding of the bone cement to articular endoprostheses to be influenced in a targeted manner.

According to a further preferred embodiment, the composition according to the invention or at least one of the pastes A, B or D can contain at least one stabiliser. The stabiliser should be suitable to prevent spontaneous polymerisation of the monomers for radical polymerisation that are contained in the paste. Moreover, the stabiliser should not undergo interfering interactions with the other ingredients contained in the paste according to the invention. Stabilisers of said type are known according to the prior art. According to a preferred embodiment, the stabiliser is 2,6-di-tert-butyl-4-methylphenol and/or 2,6-di-tert-butyl-phenol.

According to the invention, a kit shall be understood to be a system made up of at least two components. Although reference to two components (i.e. paste A and paste B) is made in the following, the kit can just as well contain more than two components, for example three, four, five or more than five components, according to need. The individual components preferably are provided to be packaged separate from each other such that the ingredients of the one kit component do not contact the ingredients of another kit component. Accordingly, it is feasible, for example, to package the respective kit components separate from each other and to store them together in a reservoir container.

Preferably, the kit is designed as a device for producing compositions for use as bone cement in appropriate manner such that it comprises a first container and a second container, whereby the first container comprises paste A and the second container comprises paste B, whereby at least one of the containers can be opened to allow paste A and paste B to be mixed after the opening, and a mixing unit for the mixing of pastes A and B. Accordingly, the kit as a device for producing the composition according to the invention can comprise a first container for powder component C and monomer component D.

Referring to the kit, for this purpose, the at least two pastes A and B are mixed with each other, upon which the composition according to the invention is obtained. The mixing ratio preferably is 0.5 to 1.5 parts by weight of paste A and 0.5 to 1.5 parts by weight of paste B. According to a particularly preferred embodiment, the fraction of paste A is 30 to 70% by weight and the fraction of paste B is 30 to 70% by weight, each relative to the total weight of pastes A and B, respectively. The mixing ratio of powder component C and monomer component D preferably is 3:1 to 1:3, in particular 2:2 party by weight. The mixing process can involve common mixing devices, for example a static mixer or a dynamic mixer.

The composition ultimately obtained is tack-free instantaneously (ISO 5833 standard) after the pastes of the kit are mixed.

The composition according to the invention can be used within 20 to 60 seconds after the composition is produced, in particular after pastes A and B or powder component C and monomer component D are mixed. The composition according to the invention is therefore non-dripping and usable very quickly from approx. 20 seconds after being produced by mixing. A common non-dripping composition according to the invention can be obtained as quickly as approx. 40 seconds after the mixing process is started. The curable composition thus produced can then be processed for approx. 8 to 9 minutes. Accordingly, the window of usability for processing of the composition was increased to approx. 8 to 9 minutes. Similar bone cements according to the prior art become non-dripping only 2 to 3 minutes after the mixing process and can then be processed only for a period of 7 minutes, whereby they, as another disadvantage, are difficult to press through a cannula since they adhere to it. Accordingly, the compositions according to the invention are advantageous in that they are rapidly usable and easier to apply within a broader time window.

The bone cement generated from the paste according to the invention or paste C by curing attains high strength approximately six to eight minutes after the pastes or components present in the kit are mixed with each other.

Another subject matter of the invention is a bone cement that can be obtained through mixing pastes A and B or powder component C and monomer component D, in particular the curable bone cement or the cured bone cement.

Another subject matter of the invention is a form body that can be obtained through polymerisation of a composition according to the invention by mixing pastes A and B or powder component C and monomer component D, and polymerisation.

The bone cements and compositions or kits according to the invention are well-suited for use during augmentation of osteoporotic bone tissue and, particularly preferably, in vertebroplasty or kyphoplasty and, particularly, for augmentation of drill holes in osteoporotic bone tissues. Also well-suited are bone cements for filling bone cavities, for femuroplasty, for vertebroplasty, for the manufacture of spacers, for mechanical fixation of articular endoprostheses, for filling skull defects or for the production of carrier materials for local antibiotics therapy or as carrier material for local release of pharmaceutically active substances.

The cement according to the invention can be introduced into the osteoporotic bone tissue through cannulated screws and, once it is cured, stabilises the connection between the bone tissue and the cannulated screws. The cement can be used not only in vertebroplasty and kyphoplasty, but also in methods derived therefrom, such as vesselplasty.

The invention is illustrated in more detail through the examples presented in the following, though without limiting the scope of the invention.

In examples 1-3 and the reference example, a polymethyl-methacrylate-co-methylacrylate (molar mass >500,000 g/mol); commercial dibenzoylperoxide (BPO, phlegmatised with 25% by weight water), Aerosil® 380 (Evonik), and glycerol-1,2,3-tri-octoate (Sigma-Aldrich) were used.

| | Composition | | | |
|---|---|---|---|---|
| Example no. | Polymer [g] | BPO 75% [mg] | Aerosil 380 [mg] | Glycerol-1,2,3-tri-octoate [g] |
| 1 | 25.90 | 98 | 50 | 1.00 |
| 2 | 25.90 | 98 | 50 | 1.50 |
| 3 | 25.90 | 98 | 50 | 2.00 |
| Reference | 25.90 | 98 | — | — |

The composition of the monomer liquid was 99.3% by weight methylmethacrylate and 0.7% by weight N,N-dimethyl-p-toluidine. The methylmethacrylate contained 10 ppm hydroquinone as stabiliser.

The powder-shaped cement compositions of examples 1-3 and the reference example were each mixed with 10 ml of monomer liquid over a period of 30 seconds. In examples 1-3, this produced a non-dripping cement dough after approx. 40 seconds that had a processing time of approx. 8-9 minutes. During said processing phase, it was feasible to press said samples through 18 G cannulas (cannula with an external diameter of 1.2 mm) by means of a 3 ml syringe without any difficulty. The cement dough showed little adhesion to the cannula. The reference cement produced a non-dripping cement dough only after a waiting period of 2-3 minutes, which then had a processing time of approx. 7 minutes. The cement dough showed pronounced adhesion to the 18 G cannula and was quite difficult to press out.

The cement dough of examples 1-3 and of the reference example produced through mixing the powder component and the monomer liquid was used to produce strip-shaped test bodies with dimensions of (75 mm×10 mm×3.3 mm) for the assay of bending strength and flexural modulus and cylindrical form bodies (diameter 6 mm, height 12 mm) were produced for the assay of compressive strength. The sample bodies were then stored for 24 hours on air at 23±1° C. Then the 4-point flexural strength, flexural modulus, and the compressive strength of the test bodies were determined using a Zwick universal testing device.

| Sample no. | 4-point flexural strength | Flexural modulus [MPa] | Compressive strength [MPa] |
|---|---|---|---|
| 1 | 60.1 ± 1.2 | 2999 ± 145 | 88.3 ± 2.0 |
| 2 | 58.3 ± 1.1 | 2851 ± 102 | 85.7 ± 2.4 |
| 3 | 45.6 ± 1.7 | 2174 ± 60 | 86.3 ± 1.9 |
| Reference | 54.9 ± 0.9 | 2741 ± 57 | 91.7 ± 0.9 |

The results of the 4-point flexural strength, flexural modulus, and compressive strength tests on cured cements 1 and 2 show that the mechanical stability requirements of ISO 5833 are met. In example 3, the flexural modulus and compressive strength requirements of ISO 5833 are met, whereas the 4-point flexural strength requirements are not. ISO 5833 defines the following parameters: 4-point flexural strength of at least 50 MPa, flexural modulus of at least 1,800 MPa, and compressive strength of at least 70 MPa.

The invention claimed is:

1. A method of augmenting osteoporotic bone tissue, said method comprising applying a bone cement into said bone tissue, wherein the bone cement is curable and comprises a composition having the following ingredients:
    a) at least one organic polymer;
    b) at least one monomer for radical polymerization;
    c) at least one polymerization initiator;
    d) at least one particulate inorganic additive having a BET surface of at least 200 $m^2$/g, wherein the additive comprises covalently bound hydroxyl groups, and wherein the composition comprises the additive in a concentration of 0.02 to 0.14% by weight, based on a total weight of the composition; and
    e) one fatty acid ester or a mixture of fatty acid esters, wherein the one fatty acid ester or mixture of fatty acid esters is liquid at room temperature, and wherein the composition comprises the one fatty acid ester or mixture of fatty acid esters in a concentration of 1.0 to 6.0% by weight, based on a total weight of the composition.

2. Method according to claim 1, wherein the composition is a thixotropic and curable fluid or a thixotropic and curable paste.

3. Method according to claim 1, wherein the at least one fatty acid ester or mixture of fatty acid esters is selected from (i) an ester from converting at least one fatty acid and a mono-alcohol, diol, triol or polyol each having 1 to 15 C atoms or a polyetherpolyol;
    (ii) a naturally occurring fatty acid ester or a fatty acid ester of natural origin; and
    (iii) a mixture containing fatty acid esters from (i) and (ii).

4. Method according to claim 1, wherein the at least one fatty acid ester or mixture of fatty acid esters is liquid at room temperature (18-25° C.) or at body temperature (approx. 36 to 37.5° C.).

5. Method according to claim 1, wherein the fatty acid ester or mixture of fatty acid esters comprises fatty acid alkyl ester(s), at least one triglyceride or a mixture thereof.

6. Method according to claim 1, wherein the fatty acid ester or the mixture of fatty acid esters comprises saturated fatty acids and/or unsaturated fatty acids.

7. Method according to claim 1, wherein the particulate inorganic additive comprises HO—Si groups that are covalently bound to the particles (silanol groups).

8. Method according to claim 1, wherein the particulate inorganic additive is selected from the group of pyrogenic silicon oxide, pyrogenic mixed metal-silicon oxides, bentonite, montmorillonite, and mixtures thereof.

9. Method according to claim 1, wherein the particulate inorganic additive comprises a pyrogenic silicon dioxide having an $SiO_2$ content of more than or equal to 99.8% by weight (of the calcined additive) and a content of chlorides and foreign metal oxides of less than or equal to 0.2% by weight relative to the additive.

10. Method according to claim 1, wherein the particulate inorganic additive is pyrogenic silicon dioxide having a BET surface of at least 300 $m^2/g$.

11. Method according to claim 1, wherein the fatty acid ester or mixtures of fatty acid esters are selected from the group of the saturated and the unsaturated fatty acid esters, whereby
(i) the group of the saturated fatty acid esters comprises esters of caprylic acid (octanoic acid), capric acid (decanoic acid), lauric acid (dodecanoic acid), myristic acid (tetradecanoic acid), palmitic acid (hexadecanoic acid), and stearic acid (octadecanoic acid), and
(ii) the group of the unsaturated fatty acid esters comprises esters of linolic acid, alpha-linolenic acid, gamma-linolenic acid, calendula acid, punicic acid, alpha-elaeostearic acid, beta-elaeostearic acid, arachidonic acid, timnodonic acid, clupanodonic acid, cervonic acid, myristoleic acid, undecylenic acid, palmitoleic acid, petroselic acid, oleic acid, elaidic acid, vaccenic acid, gadoleic acid, icosenic acid, ceteoleic acid, erucic acid, nervonic acid, whereby the esters in (i) and (ii) are derived from conversion of one or more fatty acids from (i) and/or (ii) with a mono-alcohol, diol, triol or polyol, each independently having 1 to 15 C atoms.

12. Method according to claim 1, wherein the liquid fatty acid esters are selected from:
glycerol-tri-caprylate (glycerol-tri-octoate), glycerol-tri-caprinate (glycerol-tri-decanoate), propylene glycol dicaprylate and propylene dicaprate and mixtures thereof.

13. Method according to claim 1, wherein the fatty acid esters that are liquid at room temperature are selected from:
the methyl esters, ethyl esters, n-propyl esters, isopropyl esters and glycerides of caprylic acid (octanoic acid), capric acid (decanoic acid), lauric acid (dodecanoic acid), myristic acid (tetradecanoic acid), palmitic acid (hexadecanoic acid), and stearic acid (octadecanoic acid) and mixtures thereof.

14. Method according to claim 1, wherein the organic polymer is selected from poly(alkyl-2-acrylic acid alkylester), poly(aryl-2-acrylic acid alkylester), poly(arylalkyl-2-acrylic acid alkylester), each independently having 1 to 18 C atoms in the alkyl group, each independently having 6 to 14 C atoms in the aryl group, each independently having 6 to 14 C atoms in the arylalkyl group, and each independently having 1 to 10 C atoms in the alkylester group and mixtures thereof.

15. Method according to claim 1, wherein the organic polymer comprises at least one poly(methacrylic acid methylester) (PMMA) and methacrylic acid methylester (MMA) as monomer.

16. Method according to claim 1, wherein the organic polymer is selected from the group of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), copolymers of said organic polymer, and mixtures thereof.

17. Method according to claim 1, wherein the monomer is selected from at least one alkyl-2-acrylic acid alkylester, aryl-2-acrylic acid alkylester, arylalkyl-2-acrylic acid alkylester, each independently having 1 to 18 C atoms in the alkyl group, each independently having 6 to 14 C atoms in the aryl group, each independently having 6 to 14 C atoms in the arylalkyl group, and each independently having 1 to 10 C atoms in the alkylester group and mixtures thereof.

18. The method according to claim 1, which is carried out for augmentation of osteoporotic bone tissue in vertebroplasty, kyphoplasty, or augmentation of drill holes in osteoporotic bone tissue, for filling bone cavities, for femuroplasty, for the manufacture of spacers, for mechanical fixation of articular endoprostheses, for filling skull defects or for the production of carrier materials for local antibiotics therapy or as carrier material for local release of pharmaceutically active substances.

* * * * *